(12) United States Patent
Cannon et al.

(10) Patent No.: US 9,783,795 B2
(45) Date of Patent: Oct. 10, 2017

(54) MULTI-EPITOPE PEPTIDE-LOADED DENDRITIC CELL IMMUNOTHERAPY FOR CANCER

(76) Inventors: Martin J. Cannon, Little Rock, AR (US); Kristina L. Bondurant, Little Rock, AR (US); Timothy J. O'Brien, Little Rock, AR (US)

(*) Notice: Subject to any disclaimer, the term of this patent is extended or adjusted under 35 U.S.C. 154(b) by 2074 days.

(21) Appl. No.: 12/913,174

(22) Filed: Oct. 27, 2010

(65) Prior Publication Data
US 2011/0038895 A1 Feb. 17, 2011

Related U.S. Application Data

(62) Division of application No. 11/986,352, filed on Nov. 21, 2007, now Pat. No. 7,846,446.

(60) Provisional application No. 60/860,714, filed on Nov. 22, 2006.

(51) Int. Cl.
| | |
|---|---|
| A61K 38/00 | (2006.01) |
| A61K 38/08 | (2006.01) |
| A61K 38/10 | (2006.01) |
| A61K 38/16 | (2006.01) |
| C12N 9/64 | (2006.01) |

(52) U.S. Cl.
CPC ......... *C12N 9/6445* (2013.01); *C12N 9/6424* (2013.01); *A61K 38/00* (2013.01)

(58) Field of Classification Search
CPC ........ A61K 38/00; A61K 38/08; A61K 38/10; A61K 38/16
USPC .......... 424/277.1; 514/21.7, 21.6, 21.5, 21.4, 514/21.3; 530/329, 328, 327, 326, 325, 530/324
See application file for complete search history.

(56) References Cited

U.S. PATENT DOCUMENTS

| | | | |
|---|---|---|---|
| 5,972,616 A | 10/1999 | O'Brien | |
| 6,649,741 B1 | 11/2003 | O'Brien | |
| 6,875,609 B2 | 4/2005 | O'Brien | |
| 7,030,231 B1 | 4/2006 | Craik | |
| 7,355,015 B1 * | 4/2008 | Dickson et al. | 530/388.26 |
| 2004/0018196 A1 | 1/2004 | Mezes | |
| 2004/0224891 A1 | 11/2004 | O'Brien | |
| 2006/0104979 A1 | 5/2006 | Craik | |
| 2009/0169575 A1 * | 7/2009 | Rohlff | 424/185.1 |

FOREIGN PATENT DOCUMENTS

| | | | | |
|---|---|---|---|---|
| WO | WO 00/55350 | * | 9/2000 | C12P 19/34 |
| WO | WO 2003/031585 | | 4/2003 | |
| WO | WO 2004/075713 | | 9/2004 | |
| WO | WO 2005/110459 | | 11/2005 | |

OTHER PUBLICATIONS

2000, Genbank accession No. AAG15395.
1994, Genbank accession No. AAC37551.
2008, Genbank accession No. NP_002142.
Southwood S, Sidney J, Kondo a, et al. Several common HLA-DR types share largely overlapping peptide binding repertoires. J Immunol 1998;160:3363-73.
Parker KC, Bednarek MA, Coligan JE. Scheme for ranking potential HLA-A2 binding peptides based on independent binding of individual peptide side-chains. J Immunol 1994;152:163-75.
Shi Ye, et al. Identification and characterization of a novel matrix-degrading protease from hormone-dependent human breast cancer cells. Cancer Res. 1993;53:1409-15.
Tanimoto H, et al. Transmembrane serine protease TADG-15 (ST14/matriptase/MT-SP1): expression and prognostic value in ovarian cancer. Br J Cancer. 2005; 92:278-83.
Suzuki M, et al. Inhibition of tumor invasion by genomic down-regulation of matriptase through suppression of activation of receptor-bound prourokinase. J Biol Chem. 2004; 279:14899-908.
Galkin AV, et al. CVS-3983, a selective matriptase inhibitor, suppresses the growth of androgen independent prostate tumor xenografts. Prostate. 2004; 61:228-235.
Lin CY, Anders J, Johnson M, Sang QA, Dickson RB. Molecular cloning of cDNA for matriptase, a matrix-degrading serine protease with trypsin-like activity. J Biol Chem. 1999;274:18231-6.
List, K., T.H. Bugge, R. Szabo. 2006. Matriptase: potent proteolysis on the cell surface. Mol. Med. 12:1-7.
Cannon Mj, O'Brien TJ, Underwood LJ, Crew MD, Bondurant KL, Santin AD. Novel target antigens for dendritic cell immunotherapy of ovarian cancer. Expert Rev Anticancer Ther 2002;2:89-97.
Santin AD, Cane' S, Bellone S, Bignotti E, Palmieri M, De Las Casas LE, Roman JJ, Anfossi S, O'Brien T, Pecorelli S. The serine protease stratum corneum chymotryptic enzyme (kallikrein 7) is highly overexpressed in squamous cervical cancer cells. Gynecol Oncol. Aug. 2004;94(2):283-8.
Schuler G, Schuler-Thurner B, Steinman RM. The use of dendritic cells in cancer immunotherapy. Curr Opin Immunol 2003;15:138-47.
Gilboa E. The promise of cancer vaccines. Nat Rev Cancer 2004;4:401-11.
Santin AD, Hermonat PL, Ravaggi A, Pecorelli S, Cannon Mj, Parham GP. Induction of tumor-specific HLA class I-restricted CD8+ cytotoxic T lymphocytes by ovarian tumor antigen-pulsed autologous dendritic cells in patients with advanced ovarian cancer. Am J Obstet Gynecol 2000;183:601-9.
Tanimoto H, Underwood LJ, Shigemasa K, et al. The stratum corneum chymotryptic enzyme which mediates shedding and desquamation of skin cells is highly overexpressed in ovarian tumor cells. Cancer 1999;86:2074-82.

(Continued)

*Primary Examiner* — Julie Ha
(74) *Attorney, Agent, or Firm* — Hugh McTavish

(57) ABSTRACT

Peptides of from about 7 to about 50 amino acid residues in length that have epitopes that bind to more than one HLA class II protein and stimulate CD4+ T cells for treatment of cancer from one of three serine proteases overexpressed in ovarian cancer and other cancers—stratum corneum chymotryptic enzyme, matriptase, and hepsin—are described. Since the peptides bind to more than one HLA class II protein variant, they can be used to treat cancer in most patients of a population having a variety of HLA class II alleles. The peptides can be loaded onto autologous dendritic cells of a cancer patient and infused into the patient to activate a CD4+ and CD8+ T cell response that recognizes tumor cells expressing the peptide antigen.

8 Claims, 2 Drawing Sheets

(56) References Cited

OTHER PUBLICATIONS

Santin AD, Bellone S, Ravaggi A, Pecorelli S, Cannon Mj, Parham GP. Induction of ovarian tumor-specific CD8+ cytotoxic T lymphocytes by acid-eluted peptide-pulsed autologous dendritic cells. Obstet Gynecol 2000;96:422-30.

Nazaruk RA, Rochford R, Hobbs MV, Cannon MJ. Functional diversity of the CD8+ T cell response to Epstein-Barr virus: Implications for the pathogenesis of EBV-associated lymphoproliferative disorders. Blood 1998;91:3875-83.

Rammensee H-G, Friede T, Stevanovic S. MHC-ligands and peptide motifs: first listing. Immunogenetics 1995;41:178-228.

Tanimoto H., Yan Y., Clarke J., Korourian S., Shigemasa K., Parmley T. H., Parham G. P., O'Brien T. J. Hepsin, a cell surface serine protease identified in hepatoma cells, is overexpressed in ovarian cancer. Cancer Res. 1997;57:28842887.

Dhanasekaran, S. M.; Barrette, T. R.; Ghosh, D.; Shah, R.; Varambally, S.; Kurachi, K.; Pienta, K. J.; Rubin, M. A.; Chinnaiyan, A. M. Delineation of prognostic biomarkers in prostate cancer. Nature (London). 2001;412:822-826.

Klezovitch O., Chevillet J., Mirosevich J., Roberts R. L., Matusik R. J., Vasioukhin V. Hepsin promotes prostate cancer progression and metastasis. Cancer Cell. 2004;6:185-195.

Magee, J. A.; Araki, T.; Patil, S.; Ehrig, T.; True, L.; Humphrey, P. A.; Catalona, W. J.; Watson, M. A.; Milbrandt, J. Expression profiling reveals hepsin overexpression in prostate cancer. Cancer Res. 2001;61:5692-5696.

Stamey, T. A.; Warrington, J. A.; Caldwell, M. C.; Chen, Z.; Fan, Z.; Mahadevappa, M.; McNeal, J. E.; Nolley, R.; Zhang, Z. Molecular genetic profiling of Gleason grade 4/5 prostate cancers compared to benign prostatic hyperplasia. J. Urol. 2001;166:2171-2177.

Adib, T. R.; Henderson, S.; Perrett, C.; Hewitt, D.; Bourmpoulia, D.; Ledermann, J.; Boshoff, C. Predicting biomarkers for ovarian cancer using gene-expression microarrays. Br. J. Cancer. 2004;90:686-692.

Stephan C., Yousef G. M., Scorilas a., Jung K., Jung M., Kristiansen G., Hauptmann S., Kishi T., Nakamura T., Loening S. A., Diamandis E. P. Hepsin is highly over expressed in and a new candidate for a prognostic indicator in prostate cancer. J. Urol. 2004;171:187-191.

Zacharski, L. R.; Ornstein, D. L.; Memoli, V. A.; Rousseau, S. M.; Kisiel, W. Expression of the factor VII activating protease, hepsin, in situ in renal cell carcinoma. Thromb. Haemostasis. 1998;79:876-877.

List K, Szabo R, Molinolo A, Sriuranpong V, Redeye V, Murdock T, Burke B, Nielsen BS, Gutkind JS, Bugge TH. (2005) Deregulated matriptase causes ras-independent multistage carcinogenesis and promotes ras-mediated malignant transformation. Genes Dev. 19:1934-1950.

Takeuchi, T. et al. (1999) Reverse biochemistry: Use of macromolecular protease inhibitors to dissect complex biological processes and identify a membranetype serine protease in epithelial cancer and normal tissue. Proc. Natl. Acad. Sci. USA 96:11054-11061.

Parr, C. et al. (2004) the Hepatocyte Growth Factor Regulatory Factors in Human Breast Cancer. *Clin. Cancer Res.* 10:202-211.

Rudinger J, "Characteristics of the amino acids as components of a peptide hormone sequence," Peptide Hormones, JA Parsons Edition, University Park Press, Jun. 1976, pp. 1-7.

"Designing Custom Peptides," from SIGMA Genosys, pp. 1-2. Accessed Dec. 16, 2004.

Schinzel R, Drueckes P, "The phosphate recognition site of *Escherichia coli* maltodextrin phosphorylase," FEBS, Jul. 1991, 286(1,2): 125-128.

Berendsen HJC, "A Glimpse of the Holy Grail?" Science, 1998, 282: 642-643.

Voet D, Voet JG, Biochemistry, Second Edition, John Wiley & Sons, Inc., 1995, pp. 235-241.

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.

\* cited by examiner

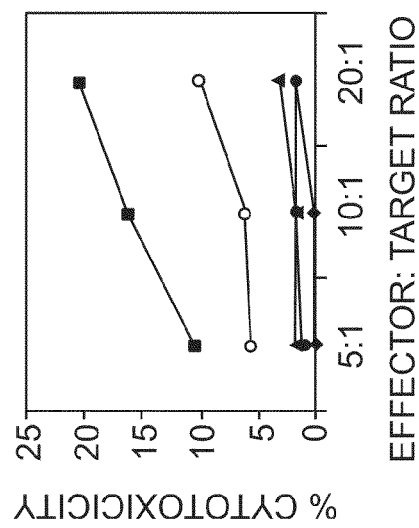
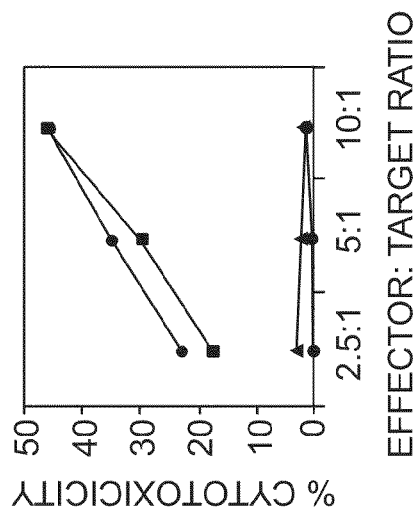
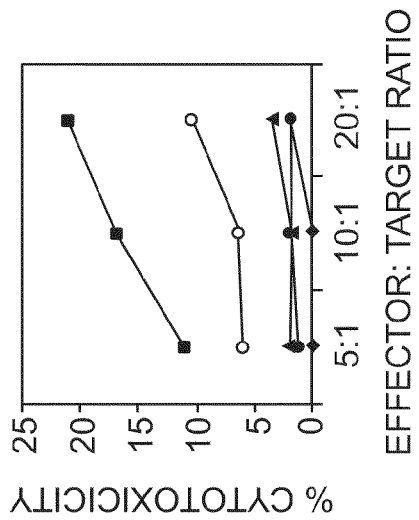
Fig. 2A
Fig. 2B
Fig. 2C

SEQUENCE LISTING

```
<160> NUMBER OF SEQ ID NOS: 17

<210> SEQ ID NO 1
<211> LENGTH: 253
<212> TYPE: PRT
<213> ORGANISM: Homo sapiens

<400> SEQUENCE: 1

Met Ala Arg Ser Leu Leu Leu Pro Leu Gln Ile Leu Leu Leu Ser Leu
1               5                   10                  15

Ala Leu Glu Thr Ala Gly Glu Glu Ala Gln Gly Asp Lys Ile Ile Asp
            20                  25                  30

Gly Ala Pro Cys Ala Arg Gly Ser His Pro Trp Gln Val Ala Leu Leu
        35                  40                  45

Ser Gly Asn Gln Leu His Cys Gly Gly Val Leu Val Asn Glu Arg Trp
    50                  55                  60

Val Leu Thr Ala Ala His Cys Lys Met Asn Glu Tyr Thr Val His Leu
65                  70                  75                  80

Gly Ser Asp Thr Leu Gly Asp Arg Arg Ala Gln Arg Ile Lys Ala Ser
                85                  90                  95

Lys Ser Phe Arg His Pro Gly Tyr Ser Thr Gln Thr His Val Asn Asp
            100                 105                 110

Leu Met Leu Val Lys Leu Asn Ser Gln Ala Arg Leu Ser Ser Met Val
        115                 120                 125

Lys Lys Val Arg Leu Pro Ser Arg Cys Glu Pro Pro Gly Thr Thr Cys
```

```
            130                 135                 140
Thr Val Ser Gly Trp Gly Thr Thr Thr Ser Pro Asp Val Thr Phe Pro
145                 150                 155                 160

Ser Asp Leu Met Cys Val Asp Val Lys Leu Ile Ser Pro Gln Asp Cys
                165                 170                 175

Thr Lys Val Tyr Lys Asp Leu Leu Glu Asn Ser Met Leu Cys Ala Gly
            180                 185                 190

Ile Pro Asp Ser Lys Lys Asn Ala Cys Asn Gly Asp Ser Gly Gly Pro
        195                 200                 205

Leu Val Cys Arg Gly Thr Leu Gln Gly Leu Val Ser Trp Gly Thr Phe
    210                 215                 220

Pro Cys Gly Gln Pro Asn Asp Pro Gly Val Tyr Thr Gln Val Cys Lys
225                 230                 235                 240

Phe Thr Lys Trp Ile Asn Asp Thr Met Lys Lys His Arg
                245                 250

<210> SEQ ID NO 2
<211> LENGTH: 417
<212> TYPE: PRT
<213> ORGANISM: Homo sapiens

<400> SEQUENCE: 2

Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Thr Ala Ile
                20                  25                  30

Gly Ala Ala Ser Trp Ala Ile Val Ala Val Leu Leu Arg Ser Asp Gln
            35                  40                  45

Glu Pro Leu Tyr Pro Val Gln Val Ser Ala Asp Ala Arg Leu Met
    50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
        115                 120                 125

Gln Arg Leu Leu Glu Val Ile Ser Val Cys Asp Cys Pro Arg Gly Arg
    130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
            180                 185                 190

Leu Ser Gly Asp Trp Val Leu Thr Ala Ala His Cys Phe Pro Glu Arg
        195                 200                 205

Asn Arg Val Leu Ser Arg Trp Arg Val Phe Ala Gly Ala Val Ala Gln
    210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255
```

```
Asp Ile Ala Leu Val His Leu Ser Ser Pro Leu Pro Leu Thr Glu Tyr
            260                 265                 270

Ile Gln Pro Val Cys Leu Pro Ala Ala Gly Gln Ala Leu Val Asp Gly
        275                 280                 285

Lys Ile Cys Thr Val Thr Gly Trp Gly Asn Thr Gln Tyr Tyr Gly Gln
    290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
                340                 345                 350

Ser Gly Gly Pro Phe Val Cys Glu Asp Ser Ile Ser Arg Thr Pro Arg
            355                 360                 365

Trp Arg Leu Cys Gly Ile Val Ser Trp Gly Thr Gly Cys Ala Leu Ala
        370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu
```

<210> SEQ ID NO 3
<211> LENGTH: 855
<212> TYPE: PRT
<213> ORGANISM: Homo sapiens

<400> SEQUENCE: 3

```
Met Gly Ser Asp Arg Ala Arg Lys Gly Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
                100                 105                 110

Phe Val Ser Leu Ala Ser Lys Val Lys Asp Ala Leu Lys Leu Leu Tyr
            115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
                180                 185                 190

Val Thr Ser Val Val Ala Phe Pro Thr Asp Ser Lys Thr Val Gln Arg
            195                 200                 205
```

```
Thr Gln Asp Asn Ser Cys Ser Phe Gly Leu His Ala Arg Gly Val Glu
    210                 215                 220
Leu Met Arg Phe Thr Thr Pro Gly Phe Pro Asp Ser Pro Tyr Pro Ala
225                 230                 235                 240
His Ala Arg Cys Gln Trp Ala Leu Arg Gly Asp Ala Asp Ser Val Leu
                245                 250                 255
Ser Leu Thr Phe Arg Ser Phe Asp Leu Ala Ser Cys Asp Glu Arg Gly
            260                 265                 270
Ser Asp Leu Val Thr Val Tyr Asn Thr Leu Ser Pro Met Glu Pro His
        275                 280                 285
Ala Leu Val Gln Leu Cys Gly Thr Tyr Pro Pro Ser Tyr Asn Leu Thr
    290                 295                 300
Phe His Ser Ser Gln Asn Val Leu Leu Ile Thr Leu Ile Thr Asn Thr
305                 310                 315                 320
Glu Arg Arg His Pro Gly Phe Glu Ala Thr Phe Phe Gln Leu Pro Arg
                325                 330                 335
Met Ser Ser Cys Gly Gly Arg Leu Arg Lys Ala Gln Gly Thr Phe Asn
            340                 345                 350
Ser Pro Tyr Tyr Pro Gly His Tyr Pro Pro Asn Ile Asp Cys Thr Trp
        355                 360                 365
Asn Ile Glu Val Pro Asn Asn Gln His Val Lys Val Ser Phe Lys Phe
    370                 375                 380
Phe Tyr Leu Leu Glu Pro Gly Val Pro Ala Gly Thr Cys Pro Lys Asp
385                 390                 395                 400
Tyr Val Glu Ile Asn Gly Glu Lys Tyr Cys Gly Glu Arg Ser Gln Phe
                405                 410                 415
Val Val Thr Ser Asn Ser Asn Lys Ile Thr Val Arg Phe His Ser Asp
            420                 425                 430
Gln Ser Tyr Thr Asp Thr Gly Phe Leu Ala Glu Tyr Leu Ser Tyr Asp
        435                 440                 445
Ser Ser Asp Pro Cys Pro Gly Gln Phe Thr Cys Arg Thr Gly Arg Cys
    450                 455                 460
Ile Arg Lys Glu Leu Arg Cys Asp Gly Trp Ala Asp Cys Thr Asp His
465                 470                 475                 480
Ser Asp Glu Leu Asn Cys Ser Cys Asp Ala Gly His Gln Phe Thr Cys
                485                 490                 495
Lys Asn Lys Phe Cys Lys Pro Leu Phe Trp Val Cys Asp Ser Val Asn
            500                 505                 510
Asp Cys Gly Asp Asn Ser Asp Glu Gln Gly Cys Ser Cys Pro Ala Gln
        515                 520                 525
Thr Phe Arg Cys Ser Asn Gly Lys Cys Leu Ser Lys Ser Gln Gln Cys
    530                 535                 540
Asn Gly Lys Asp Asp Cys Gly Asp Gly Ser Asp Glu Ala Ser Cys Pro
545                 550                 555                 560
Lys Val Asn Val Val Thr Cys Thr Lys His Thr Tyr Arg Cys Leu Asn
                565                 570                 575
Gly Leu Cys Leu Ser Lys Gly Asn Pro Glu Cys Asp Gly Lys Glu Asp
            580                 585                 590
Cys Ser Asp Gly Ser Asp Glu Lys Asp Cys Asp Cys Gly Leu Arg Ser
        595                 600                 605
Phe Thr Arg Gln Ala Arg Val Val Gly Gly Thr Asp Ala Asp Glu Gly
    610                 615                 620
Glu Trp Pro Trp Gln Val Ser Leu His Ala Leu Gly Gln Gly His Ile
```

```
            625                 630                 635                 640
Cys Gly Ala Ser Leu Ile Ser Pro Asn Trp Leu Val Ser Ala Ala His
            645                 650                 655
Cys Tyr Ile Asp Asp Arg Gly Phe Arg Tyr Ser Asp Pro Thr Gln Trp
            660                 665                 670
Thr Ala Phe Leu Gly Leu His Asp Gln Ser Gln Arg Ser Ala Pro Gly
            675                 680                 685
Val Gln Glu Arg Arg Leu Lys Arg Ile Ile Ser His Pro Phe Phe Asn
            690                 695                 700
Asp Phe Thr Phe Asp Tyr Asp Ile Ala Leu Leu Glu Leu Glu Lys Pro
705                 710                 715                 720
Ala Glu Tyr Ser Ser Met Val Arg Pro Ile Cys Leu Pro Asp Ala Ser
                    725                 730                 735
His Val Phe Pro Ala Gly Lys Ala Ile Trp Val Thr Gly Trp Gly His
            740                 745                 750
Thr Gln Tyr Gly Gly Thr Gly Ala Leu Ile Leu Gln Lys Gly Glu Ile
            755                 760                 765
Arg Val Ile Asn Gln Thr Thr Cys Glu Asn Leu Leu Pro Gln Gln Ile
            770                 775                 780
Thr Pro Arg Met Met Cys Val Gly Phe Leu Ser Gly Gly Val Asp Ser
785                 790                 795                 800
Cys Gln Gly Asp Ser Gly Gly Pro Leu Ser Ser Val Glu Ala Asp Gly
                    805                 810                 815
Arg Ile Phe Gln Ala Gly Val Val Ser Trp Gly Asp Gly Cys Ala Gln
            820                 825                 830
Arg Asn Lys Pro Gly Val Tyr Thr Arg Leu Pro Leu Phe Arg Asp Trp
            835                 840                 845
Ile Lys Glu Asn Thr Gly Val
            850                 855

<210> SEQ ID NO 4
<211> LENGTH: 35
<212> TYPE: PRT
<213> ORGANISM: Homo sapiens

<400> SEQUENCE: 4

Glu Arg Val Met Ala Glu Glu Arg Val Val Met Leu Pro Pro Arg Ala
1               5                   10                  15
Arg Ser Leu Lys Ser Phe Val Val Thr Ser Val Val Ala Phe Pro Thr
            20                  25                  30
Asp Ser Lys
        35

<210> SEQ ID NO 5
<211> LENGTH: 24
<212> TYPE: PRT
<213> ORGANISM: Homo sapiens

<400> SEQUENCE: 5

Ser Asp Leu Val Thr Val Tyr Asn Thr Leu Ser Pro Met Glu Pro His
1               5                   10                  15
Ala Leu Val Gln Leu Cys Gly Thr
            20

<210> SEQ ID NO 6
<211> LENGTH: 36
<212> TYPE: PRT
```

<213> ORGANISM: Homo sapiens

<400> SEQUENCE: 6

Ser Gln Asn Val Leu Leu Ile Thr Leu Ile Thr Asn Thr Glu Arg Arg
1               5                   10                  15
His Pro Gly Phe Glu Ala Thr Phe Phe Gln Leu Pro Arg Met Ser Ser
            20                  25                  30
Cys Gly Gly Arg
        35

<210> SEQ ID NO 7
<211> LENGTH: 21
<212> TYPE: PRT
<213> ORGANISM: Homo sapiens

<400> SEQUENCE: 7

Lys Val Ser Phe Lys Phe Phe Tyr Leu Leu Glu Pro Gly Val Pro Ala
1               5                   10                  15
Gly Thr Cys Pro Lys
            20

<210> SEQ ID NO 8
<211> LENGTH: 37
<212> TYPE: PRT
<213> ORGANISM: Homo sapiens

<400> SEQUENCE: 8

Gln Glu Pro Leu Tyr Pro Val Gln Val Ser Ser Ala Asp Ala Arg Leu
1               5                   10                  15
Met Val Phe Asp Lys Thr Glu Gly Thr Trp Arg Leu Leu Cys Ser Ser
            20                  25                  30
Arg Ser Asn Ala Arg
        35

<210> SEQ ID NO 9
<211> LENGTH: 28
<212> TYPE: PRT
<213> ORGANISM: Homo sapiens

<400> SEQUENCE: 9

Cys Glu Glu Met Gly Phe Leu Arg Ala Leu Thr His Ser Glu Leu Asp
1               5                   10                  15
Val Arg Thr Ala Gly Ala Asn Gly Thr Ser Gly Phe
            20                  25

<210> SEQ ID NO 10
<211> LENGTH: 17
<212> TYPE: PRT
<213> ORGANISM: Homo sapiens

<400> SEQUENCE: 10

Phe Arg Glu Trp Ile Phe Gln Ala Ile Lys Thr His Ser Glu Ala Ser
1               5                   10                  15
Gly

<210> SEQ ID NO 11
<211> LENGTH: 23
<212> TYPE: PRT
<213> ORGANISM: Homo sapiens

<400> SEQUENCE: 11

Arg Trp Arg Val Phe Ala Gly Ala Val Ala Gln Ala Ser Pro His Gly
1               5                   10                  15

Leu Gln Leu Gly Val Gln Ala
            20

<210> SEQ ID NO 12
<211> LENGTH: 34
<212> TYPE: PRT
<213> ORGANISM: Homo sapiens

<400> SEQUENCE: 12

Gln Val Ser Leu Arg Tyr Asp Gly Ala His Leu Cys Gly Gly Ser Leu
1               5                   10                  15

Leu Ser Gly Asp Trp Val Leu Thr Ala Ala His Cys Phe Pro Glu Arg
            20                  25                  30

Asn Arg

<210> SEQ ID NO 13
<211> LENGTH: 33
<212> TYPE: PRT
<213> ORGANISM: Homo sapiens

<400> SEQUENCE: 13

Ser Asn Asp Ile Ala Leu Val His Leu Ser Ser Pro Leu Pro Leu Thr
1               5                   10                  15

Glu Tyr Ile Gln Pro Val Cys Leu Pro Ala Ala Gly Gln Ala Leu Val
            20                  25                  30

Asp

<210> SEQ ID NO 14
<211> LENGTH: 25
<212> TYPE: PRT
<213> ORGANISM: Homo sapiens

<400> SEQUENCE: 14

Ser Pro His Gly Leu Gln Leu Gly Val Gln Ala Val Val Tyr His Gly
1               5                   10                  15

Gly Tyr Leu Pro Phe Arg Asp Pro Asn
            20                  25

<210> SEQ ID NO 15
<211> LENGTH: 23
<212> TYPE: PRT
<213> ORGANISM: Homo sapiens

<400> SEQUENCE: 15

Met Ala Arg Ser Leu Leu Leu Pro Leu Gln Ile Leu Leu Leu Ser Leu
1               5                   10                  15

Ala Leu Glu Thr Ala Gly Glu
            20

<210> SEQ ID NO 16
<211> LENGTH: 24
<212> TYPE: PRT
<213> ORGANISM: Homo sapiens

<400> SEQUENCE: 16

Asn Glu Arg Trp Val Leu Thr Ala Ala His Cys Lys Met Asn Glu Tyr
1               5                   10                  15

Thr Val His Leu Gly Ser Asp Thr
            20

```
<210> SEQ ID NO 17
<211> LENGTH: 18
<212> TYPE: PRT
<213> ORGANISM: Homo sapiens

<400> SEQUENCE: 17

Thr Cys Thr Val Ser Gly Trp Gly Thr Thr Thr Ser Pro Asp Val Thr
1               5                   10                  15

Phe Pro
```

MULTI-EPITOPE PEPTIDE-LOADED DENDRITIC CELL IMMUNOTHERAPY FOR CANCER This patent application is a divisional application under 35 U.S.C. §120 and §121 of U.S. patent application Ser. No. 11/986,352, filed Nov. 21, 2007 now U.S. Pat. No. 7,846,446, which in turn claims the benefit of priority under 35 U.S.C. 119(e) from U.S. provisional patent application Ser. No. 60/860,714, filed Nov. 22, 2006.

GOVERNMENT SUPPORT

This invention was made with government support under grants R01 CA 098927 and R41 CA 108257 awarded by the United States National Institutes of Health. The government has certain rights in the invention.

BACKGROUND OF THE INVENTION

Ovarian cancer ranks fifth among malignancies affecting women in the United States. The onset of ovarian cancer is insidious and the symptoms are nonspecific, such that two-thirds of women present with advanced disease at diagnosis. Although the initial response rate of patients with advanced disease after treatment with platinum and taxol is 73% to 77%, a large majority develop recurrent disease. These factors contribute to ovarian cancer having the highest mortality rate of all gynecologic tumors. Thus, alternative methods for treatment are a priority for ovarian cancer.

The identification of ovarian tumor-specific antigens that can serve as targets for CD8+ cytotoxic T lymphocytes (CTLs) (9) and the harnessing of dendritic cells that possess the ability to induce CTL responses to those targets (11, 12) suggests that dendritic cell immunotherapy may be of potential therapeutic benefit. Monocyte-derived dendritic cells loaded with tumor lysate antigen can induce tumor-specific CTL lysis of autologous tumor cells from patients with ovarian cancer or uterine serous papillary carcinoma (13, 14), and dendritic cells pulsed with peptides acid-eluted from HLA class I on the surface of ovarian tumor cells can stimulate CTL killing of autologous tumor (16).

The identification of appropriate tumor-specific antigens is a critical component for the development of successful ovarian tumor-specific immunotherapy.

Tumor-associated serine proteases are involved in many biological functions of cancer cells, including activation of growth and angiogenic factors and promotion of invasion and metastasis. Among the serine proteases overexpressed in some cancers is stratum corneum chymotryptic enzyme. Stratum corneum chymotryptic enzyme (SCCE), also known as kallikrein 7, is a serine protease that is overexpressed by ovarian cancer cells but not expressed by normal ovaries or other normal adult tissues, except the outermost cornified layer of the skin (15). Immunohistochemical analysis of 14 ovarian tumors showed positive staining localized to the cytoplasm and cell membrane, suggesting that SCCE may be expressed as both secreted and membrane forms (15). Quantitative RT-PCR revealed SCCE expression in >88% of serous ovarian tumors, 100% of endometrioid and clear cell tumors, but only 29% (two of seven) of mucinous tumors (15). SCCE is also overexpressed in cervical cancer (10).

Hepsin is a transmembrane serine protease that is overexpressed in prostate cancer and ovarian cancer, as well as renal cell carcinoma (19-26). In at least one report its overexpression was linked to metastasis and tumor progression (21).

Matriptase (also known as TADG-15) is a transmembrane serine protease that was discovered in 1993 and cloned in 1999 (3, 7). It is overexpressed in many tumors of epithelial origin, including carcinomas of the head and neck, mesothelium, breast, ovary, cervix, prostate, lung, and gastrointestinal tract, as well as in cell lines derived from these tumors (8). Its expression has been linked to increased tumor invasiveness (5-6). It is expressed in a high percentage of ovarian carcinomas but not in normal ovary tissue (4).

New treatments for ovarian and other cancers are needed. New targets for cancer immunotherapy are needed.

SUMMARY OF THE INVENTION

The invention involves peptides of from about 7 to about 50 amino acid residues in length that have epitopes that bind to more than one HLA class II protein and stimulate CD4+ T cells for treatment of cancer. CD4+ T cells have the CD4 antigen on their surface and are also known as helper T cells. CD4+ T cells activate the response of other cells in the immune system, including antibody-producing B cells and cytotoxic CD8+ T cells. CD8+ T cells, also known as cytotoxic T lymphocyctes (CTL), are the cells primarily responsible for directly killing cancer cells when an immune response is raised to cancer cells. But CD4+ T cells are crucial to activate the CD8+ T cell response and crucial for maintaining long-term immune memory that will recognize cancer cells in the future to prevent disease recurrence. CD4+ T cells may also have the ability to kill tumor cells directly without CD8+ T cells.

Antigens are presented as short peptides bound to HLA class I or class II proteins on the surface of target cells for recognition by T cells. CD8+ T cells recognize antigenic peptides bound to HLA class I proteins. CD4+ T cells recognize antigenic peptides bound to HLA class II proteins. There are several variants of HLA class I and class II proteins (expressed from different alleles), and peptides that bind to one HLA class I or class II protein may not bind to other variants. This makes it difficult to select universal peptides that will activate an immune response in all or most individuals in a population.

The inventors have utilized an algorithm to predict peptides that will bind to three common HLA class II variant proteins (1). Peptides that bind to these variants are also likely to bind to other HLA class II variants (1). The invention involves the selection of peptides from serine proteases overexpressed in tumor cells—namely SCCE, hepsin, and matriptase—that have at least one epitope predicted to bind to HLA class II alleles and the identification of peptides that activate CD4+ T cells, preferably CD4+ T cells from a plurality of persons having different HLA class II alleles.

Preferably the peptides have a cluster of more than one epitope predicted to bind to HLA class II allelic variants. The inventors have tested peptides containing at least one epitope predicted to bind to HLA class II allelic variants and identified peptides that activate CD4+ T cells from all the volunteers tested. Although the epitopes that bind to HLA class I proteins to activate CD8+ T cells can be different from those that bind to HLA class II proteins, the peptides tested also activated CD8+ T cells.

Thus, one embodiment of the invention comprises a purified peptide of 7-50 amino acid residues comprising an antigenic matriptase sequence (or hepsin sequence) of 7-50 amino acid residues; wherein when the purified peptide is contacted with dendritic cells to generate peptide-loaded dendritic cells and the peptide-loaded dendritic cells are contacted with T cells, the peptide-loaded dendritic cells activate CD4+ T cells (helper T cells) that recognize the matriptase (or hepsin) sequence.

Another embodiment of the invention provides a method of treating cancer that involves: (a) contacting dendritic cells with a purified peptide of 7-50 amino acid residues comprising an antigenic matriptase sequence (or hepsin sequence) of 7-50 amino acid residues; (b) contacting the peptide-loaded dendritic cells with T cells to amplify CD8+ T cells and CD4+ T cells that recognize the antigenic matriptase (or hepsin) sequence; and (c) contacting the amplified CD8+ T cells with cancer cells expressing matriptase (or hepsin) to kill the cancer cells.

Another embodiment of the invention provides a composition comprising: purified dendritic cells loaded ex vivo with a purified peptide of 7-50 amino acid residues comprising an antigenic matriptase sequence (or hepsin sequence) of 7-50 amino acid residues; wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the matriptase (or hepsin) sequence.

Another embodiment of the invention provides a method of treating cancer that involves: (a) contacting dendritic cells with a peptide comprising an antigenic matriptase sequence (or hepsin sequence) of at least 7 amino acid residues; (b) contacting the peptide-loaded dendritic cells with T cells to amplify CD8+ T cells and CD4+ T cells that recognize the antigenic matriptase (or hepsin) sequence; and (c) contacting the amplified CD8+ T cells with cancer cells expressing matriptase (or hepsin) to kill the cancer cells.

Another embodiment of the invention provides a composition comprising: purified dendritic cells loaded ex vivo with a peptide comprising an antigenic matriptase sequence (or hepsin sequence) of at least 7 amino acid residues; wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the matriptase sequence.

The invention also involves peptides, methods, and dendritic cell compositions involving SCCE peptides.

One embodiment of the invention provides a purified peptide of 7-50 amino acid residues comprising an antigenic stratum corneum chymotryptic enzyme (SCCE) sequence of 7-50 amino acid residues; wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the SCCE sequence. The antigenic SCCE sequence is SEQ ID NO:15 (residues 1-23 of SCCE), SEQ ID NO:16 (residues 61-84), SEQ ID NO:17 (residues 143-160), or a fragment thereof.

Another embodiment provides a method of treating cancer comprising: (a) contacting dendritic cells with a purified peptide of 7-50 amino acid residues comprising an antigenic SCCE sequence of 7-50 amino acid residues; (b) contacting the peptide-loaded dendritic cells with T cells to amplify CD8+ T cells and CD4+ T cells that recognize the antigenic SCCE sequence; and (c) contacting the amplified CD8+ T cells with cancer cells expressing SCCE to kill the cancer cells. The antigenic SCCE sequence is SEQ ID NO:15 (residues 1-23 of SCCE), SEQ ID NO:16 (residues 61-84), SEQ ID NO:17 (residues 143-160), or a fragment thereof.

Another embodiment of the invention provides a composition comprising: purified dendritic cells loaded ex vivo with a purified peptide of 7-50 amino acid residues comprising an antigenic SCCE sequence of 7-50 amino acid residues; wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the SCCE sequence. The antigenic SCCE sequence is SEQ ID NO:15 (residues 1-23 of SCCE), SEQ ID NO:16 (residues 61-84), SEQ ID NO:17 (residues 143-160), or a fragment thereof.

Another embodiment of the invention provides a method of treating cancer comprising: (a) contacting dendritic cells with a peptide comprising an antigenic SCCE sequence of at least 7 amino acid residues; (b) contacting the peptide-loaded dendritic cells with T cells to amplify CD8+ T cells and CD4+ T cells that recognize the antigenic SCCE sequence; and (c) contacting the amplified CD8+ T cells with cancer cells expressing SCCE to kill the cancer cells. The antigenic SCCE sequence is SEQ ID NO:15 (residues 1-23 of SCCE), SEQ ID NO:16 (residues 61-84), SEQ ID NO:17 (residues 143-160), or a fragment thereof.

Another embodiment of the invention provides a composition comprising: purified dendritic cells loaded ex vivo with a peptide comprising an antigenic SCCE sequence of at least 7 amino acid residues; wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the SCCE sequence. The antigenic SCCE sequence is SEQ ID NO:15 (residues 1-23 of SCCE), SEQ ID NO:16 (residues 61-84), SEQ ID NO:17 (residues 143-160), or a fragment thereof.

BRIEF DESCRIPTION OF THE FIGURES

FIG. 2. SCCE peptide-specific CD8+ CTL responses. Peripheral blood T cells from a volunteer donor were stimulated with dendritic cells loaded with SCCE peptides 1-23 (panel A), 61-84 (panel B), or 143-160 (panel C), and tested for lysis against LCL loaded with the respective peptide. Targets were peptide-loaded autologous lymphoblastoid cell line cells (LCL) (■), peptide-pulsed HLA A2.1-matched allogeneic LCL (●), and peptide-pulsed HLA B27-matched allogeneic LCL (○), peptide-loaded B40-matched allogeneic LCL (▲), and peptide-loaded HLA class 1-mismatched LCL (♦). Control unpulsed LCL were not lysed (data not shown).

DETAILED DESCRIPTION

Definitions

Figure 1A:
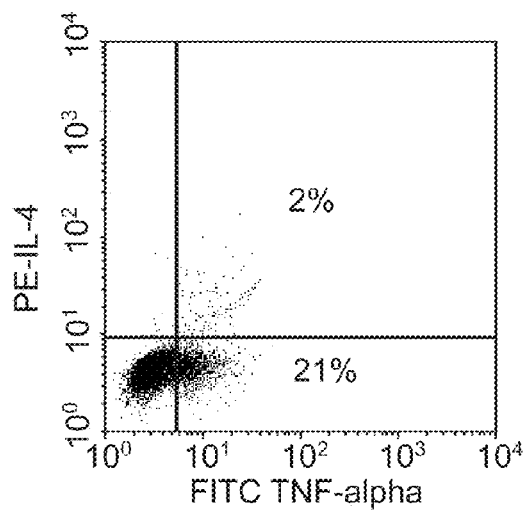
FIG. 1. Intracellular TNFα and IL-4 expression by CD4+ T cells specific for SCCE 1-23 (panel A), 61-84 (panel B), and 143-160 (panel C). Peptide-specific CD4+ T cells were stimulated overnight with peptide-loaded autologous LCL and analyzed by flow cytometry.

The term "peptide" as used herein can refer to peptides of any suitable length, up to full-length proteins, unless a length limitation is specified.

CD4+ or CD8+ T cells are considered to "recognize" a particular sequence if the CD4+ or CD8+ T cells show a response when contacted with antigen-presenting cells or target cells pulsed with a peptide consisting of the sequence. The response may be cytolysis of target cells pulsed with the peptide consisting of the sequence, or cytokine release or amplification in response to contacting antigen-presenting cells pulsed with the peptide consisting of the sequence.

Description

The invention involves peptides, preferably of from about 7 to about 50 amino acid residues in length, that have epitopes that collectively or individually bind to more than one HLA class II protein for stimulation of CD4+ T cells, and the use of the peptides for treatment of cancer. The peptides are derived from one of three serine proteases overexpressed on ovarian cancer cells and other cancer cells—SCCE, hepsin, and matriptase. Preferably the peptides have more than one epitope that binds to HLA class II protein variants. The presence of multiple epitopes allows greater confidence that the peptide will activate a CD4+ T cell response in a broad cross section of the population and not be limited to persons with particular HLA class II alleles. Preferably the peptide contains sequence segments that collectively or individually are predicted by the algorithms disclosed herein to bind to at least two, more preferably all three, of the HLA class II allelic gene products DRB*0401, DRB*0101, and DRB1*0701.

To select the peptides it is not necessary to use algorithms to predict whether any sequence in the peptide binds to HLA class I alleles. The inventors have found that the majority of the peptides are able to activate a peptide-specific CD8+ T cell response, indicating the peptides contain antigenic sequences that bind to HLA class I proteins, and probably to multiple HLA class I proteins.

The HLA class II peptide-binding site holds peptides of 12-15 amino acid residues in length. The algorithm used to predict the peptides binding to the HLA class II proteins calculates binding for a 9-amino-acid motif. 9-mer peptides or even shorter peptides can bind to class II alleles in some cases. But preferably, the peptides contain an extension of at least 3 amino acid residues on each end of a predicted 9-mer HLA class II binding sequence and are at least 15 amino acid residues in length.

Peptides to screen for use in the invention were selected by processing the sequences of SCCE, hepsin, and matriptase with an algorithm that predicts 9-mer sequences that bind to three HLA class II proteins. Extended peptides containing multiple 9-mer epitope sequences predicted to bind to the HLA class II proteins were preferentially selected for testing. The multiple 9-mer predicted epitope sequences may be overlapping or non-overlapping in the peptides. The peptides were limited in length to about 40 amino acid residues to avoid including sequences that may be present in other proteins and lead to an immune response targeted to other proteins in the body.

The peptides of the invention are preferably portions of the complete proteins. Preferably the peptides are 7-60 amino acid residues, more preferably 7-50, more preferably 9-50, more preferably 9-40 amino acid residues in length. In specific embodiments, the peptides are 7-40, 9-40, 12-40, 15-40, or 20-40 amino acid residues in length. In other specific embodiments, the peptides are 7-50, 9-50, 12-50, 15-50, or 20-50 amino acid residues in length.

The invention includes peptides comprising an antigenic matriptase, hepsin, or SCCE sequence of at least 7 amino acid residues, wherein the peptide can be used to amplify CD4+ T cells that recognize the antigenic matriptase, hepsin, or SCCE sequence. Preferably, when the peptide is contacted with dendritic cells to generate peptide-loaded dendritic cells and the peptide-loaded dendritic cells are contacted with T cells, the peptide-loaded dendritic cells also amplify CD8+ T cells that recognize the matriptase, hepsin, or SCCE sequence.

Preferably, the amplified CD8+ T cells kill autologous cancer cells expressing matriptase, hepsin, or SCCE. Preferably the killing is dependent on the cell's expressing matriptase, hepsin, or SCCE, which can be assayed by comparing killing of control autologous cells that do not express the protein.

Preferably, the peptide is able to activate CD4+ T cells in most persons of a population, i.e., has an epitope or epitopes able to bind to more than one HLA class II protein. This can be shown by showing a peptide-specific CD4+ T cell response in two different donors having no HLA class II alleles in common. The CD4+ T cell response can be proliferation, cytokine release, or cytolysis. HLA typing is routinely carried out by clinical laboratories and blood banks.

In particular embodiments, the peptides can be used with dendritic cells to activate CD4+ T cells from at least two donors with no HLA class II alleles in common.

In a particular embodiment, the purified matriptase (or hepsin or SCCE) peptide contains two antigenic matriptase (or hepsin or SCCE) sequences wherein CD4+ T cells from one of the donors recognizes one antigenic sequence and CD4+ T cells from the other donor recognizes the other antigenic matriptase sequence.

In a particular embodiment the purified peptide comprises two antigenic matriptase (or hepsin or SCCE) sequences wherein one of the two different lines of CD4+ T cells recognizes one antigenic sequence and the other CD4+ T cell line recognizes the other antigenic sequence.

In a particular embodiment, CD8+ T cells amplified with the peptide perform peptide-dependent lysis of at least two lines of target allogeneic cells pulsed with the peptide, wherein the two lines of target allogeneic cells are matched to the CD8+ T cells in different and non-overlapping HLA class I alleles.

In a more specific embodiment, the purified peptide comprises two matriptase (or SCCE or hepsin) epitopes, wherein the CD8+ T cells recognize one matriptase (or SCCE or hepsin) epitope on one target allogeneic cell line and the other matriptase (or SCCE or hepsin) epitope on the other target allogeneic cell line.

The matriptase peptides that have been tested (Example 3 below) are SEQ ID NO:4 (residues 170-204 of matriptase, SEQ ID NO:3), SEQ ID NO:5 (residues 273-296 of matriptase), SEQ ID NO:6 (residues 308-343 of matriptase) and SEQ ID NO:7 (residue 379-399 of matriptase). All of these peptides amplify CD4+ T cells that recognize the peptide. Thus, in particular embodiments, the peptide comprises one of these sequences or an antigenic fragment of one of these sequences.

The hepsin peptides that have been tested are SEQ ID NO:8 (residues 48-84 of hepsin, SEQ ID NO:2), SEQ ID NO:9 (residues 90-117 of hepsin), SEQ ID NO:10 (residues 396-412 of hepsin), SEQ ID NO:11 (residues 214-236 of hepsin), SEQ ID NO:12 (residues 177-210 of hepsin), SEQ ID NO:13 (residues 255-287 of hepsin), and SEQ ID NO:14 (residues 226-250 of hepsin). All of these peptides amplify CD4+ T cells that recognize the peptide. Thus, in particular embodiments, the peptide comprises one of these sequences or an antigenic fragment of one of these sequences.

The SCCE peptides that have been tested are SEQ ID NO:15 (residues 1-23 of SCCE, SEQ ID NO:1), SEQ ID NO:16 (residues 61-84 of SCCE), and SEQ ID NO:17 (residues 143-160 of SCCE). All of these peptides amplify CD4+ T cells that recognize the peptide. Thus, in particular embodiments, the peptide comprises one of these sequences or an antigenic fragment of one of these sequences.

Another embodiment of the invention provides a method of treating cancer that involves: (a) contacting dendritic cells with a peptide comprising an antigenic matriptase sequence (or hepsin or SCCE sequence) of at least 7 amino acid residues; (b) contacting the peptide-loaded dendritic cells with T cells to amplify CD8+ T cells and CD4+ T cells that recognize the antigenic matriptase (or hepsin or SCCE) sequence; and (c) contacting the amplified CD8+ T cells with cancer cells expressing matriptase (or hepsin or SCCE) to kill the cancer cells.

This can be performed as described in Example 4 below. If a patient's tumor is positive for any one of matriptase, SCCE, or hepsin, she can be treated with dendritic cells loaded with one peptide from the appropriate protein or with a mixture of peptides from the protein. A patient whose tumor is positive for at least two of matriptase, hepsin, and SCCE can also be treated with dendritic cells contacted with a mixture of peptides including peptides from the appropriate two or all three of matriptase, hepsin, and SCCE.

Typically to treat patients, dendritic cells would be matured ex vivo in contact with the peptides, and then the dendritic cells would be infused into the patient. In vivo the dendritic cells would amplify CD8+ T cells that would recognize and kill the tumor cells and/or CD4+ T cells that would support this response and/or kill the tumor cells directly. However, the dendritic cells could also be used to amplify CD4+ and/or CD8+ T cells specific for the peptides ex vivo, and the amplified T cells could be infused into the patient.

The dendritic cells are typically autologous.

Ex vivo amplified CD4+ and CD8+ T cells if used to treat a cancer patient typically would be autologous.

Another embodiment of the invention provides a composition comprising: purified dendritic cells loaded ex vivo with a peptide comprising an antigenic matriptase (or SCCE or hepsin) sequence of at least 7 amino acid residues; wherein when the peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the matriptase (or SCCE or hepsin) sequence. The dendritic cells can be prepared, for example, as described in Example 4 below.

The following examples are intended to illustrate the invention but not limit its scope.

EXAMPLES

Example 1. Stratum Corneum Chymotryptic Enzyme (SCCE)

SCCE, also known as kallikrein 7, is a serine protease that is overexpressed by ovarian cancer cells but not by normal ovaries or other normal adult tissues, except the outermost cornified layer of the skin (15). Immunohistochemical analysis of 14 ovarian tumors showed positive staining localized to the cytoplasm and cell membrane, suggesting that SCCE may be expressed as both secreted and membrane forms (15). Quantitative RT-PCR revealed SCCE expression in >88% of serous ovarian tumors, 100% of endometrioid and clear cell tumors, but only 29% (two of seven) mucinous tumors (15). SCCE is also overexpressed in cervical cancer (10).

The tightly limited tissue distribution of SCCE and overexpression in ovarian tumors suggests that it would be a favorable target antigen for immunotherapy. In this Example, we used computer algorithms to select several extended SCCE peptides predicted to have epitopes that bind to multiple HLA class II allelic proteins. The extended peptides were tested when loaded onto dendritic cells for amplification of CD4+ T cells and CD8+ T cells.

1. Calculation of Peptide Binding Affinity to HLA Class II and Class I Proteins.

The sequence of SCCE was scanned to calculate the predicted binding affinity of 9-mer peptides within SCCE for three common HLA class II allelic proteins—DRB*0401, DRB*0101, and DRB1*0701, using algorithms reported in reference (1). To develop the algorithms, a adjusted relative binding (ARB) value was assigned to each amino acid in each of the 9 positions of a 9-mer based on the experimentally determined binding affinity of 384 test peptides to each of the three HLA class II allelic proteins tested. All the test peptides contained a hydrophobic residue at position p1 and an small uncharged side chain residue at position p6. To develop the algorithms, it was assumed that each individual side chains bind independently. When residue R occurs at position i in the peptide, it is assumed to contribute a constant amount $R_i$ to the free energy of binding irrespective of the sequence of the rest of the peptide. For all i positions, the geometric mean of the average relative binding (ARB) of all peptides carrying R is calculated relative to the remainder of the group and used as an estimate of Ri. The algorithms calculate a binding affinity value of a hypothetical 9-mer peptide by multiplying the ARB values of each residue of the peptides. The ARB values of each amino acid residue at each position in a peptide for the DRB1*0401, DRB1*0101, and DRB1*0701 are shown in reference 1, which is hereby incorporated by reference.

It has been experimentally determined that peptides that bind to at least two of the class II alleles DRB1*0401, DRB1*0101, and DRB1*0701, are also more likely to bind to several other class II alleles, including DRB5*0101, DRB1*1501, BRB1*0901, and DRB1*1302 than peptides that bind to one or fewer of DRB1*0401, DRB1*0101, and DRB1*0701. Thus, these algorithms predict peptides that will activate CD4+ cells in most individuals of the population.

SCCE was scanned to identify extended peptide sequences of up to 40 residues in SCCE that have clusters of predicted HLA class II binding epitopes.

Optionally, the sequences can be further processed to determine whether the peptides also have sequences predicted to bind to HLA class I molecules. HLA-A2.1 is the most common HLA class I allele. Peptides with the potential to bind to HLA-A2.1 can be predicted by two computer programs. The first is at bimas.dcrt.nih.gov/molbio/hla_bind (2) and the second at the website 134.2.96.221/scripts/hlaserver.dll/EpPredict.htm (3).

2. CD4+ T Cell and CD8+ T Cell Responses to the SCCE Peptides.

SCCE peptides 1-23, 61-84, and 143-160 were synthesized. The peptides were loaded onto dendritic cells or other antigen presenting cells and used to amplify CD4+ T cells and CD8+ T cells. The amplified T cells were then tested for peptide-specific cytokine release, cellular proliferation, or cytolysis of target cells carrying the peptide.

2A. Materials and Methods:

Cell Lines, Antibodies, and Cytokines.

K562, lymphoblastoid cell lines, and HLA class I-negative C1R cells were grown in RPMI supplemented with 10% FCS, 50 µM 2-β-mercaptoethanol, 3 mmol/L L-glutamine, 100 IU/mL penicillin, and 100 µg/mL streptomycin (RPMI/10). Macrophages and dendritic cells were grown in AIM-V (Invitrogen). T cells were grown in RPMI supplemented with 10% human AB serum (Valley Biomedical, Winchester, Va.), 50 µM 2-β-mercaptoethanol, 3 mmol/L L-glutamine, 100 IU/mL penicillin, and 100 µg/mL streptomycin (RPMI/10 Hu).

Fluorochrome-conjugated anti-CD4 monoclonal antibody (MAb), anti-CD8 and anti-IL-10 were purchased from Caltag (Burlingame, Calif.). Fluorochrome-conjugated MAb specific for interleukin (IL)-4, IFN-γ, IL-13, tumor necrosis factor-α, and IL-2 were purchased from BD Immunocytometry (San Jose, Calif.). W6/32 (anti-HLA class I), L243 (anti-HLA class II), and BB7.2 (anti-HLA-A2.1) MAb were prepared from hybridomas purchased from the American Type Culture Collection.

Cytokines for the establishment of dendritic cells and T cell cultures included granulocyte macrophage colony-stimulating factor (Immunex, Seattle, Wash.), IL-4, tumor necrosis factor-α (both from R&D Systems, Minneapolis, Minn.), prostaglandin E2 (Sigma, St. Louis, Mo.), IL-1β, and IL-2 (both from the Biological Response Modifiers Program, National Cancer Institute).

Dendritic Cells and Stratum Corneum Chymotryptic Enzyme—Specific T Cells.

Peripheral blood was drawn from healthy adult volunteer donors, following an Institutional Review Board-approved protocol. Peripheral blood mononuclear cells were recovered by gradient centrifugation (Lymphoprep; Greiner Bio-One, Longwood, Fla.).

For preparation of dendritic cells, peripheral blood mononuclear cells were placed in six-well plates (Costar, Cambridge, Mass.) at a concentration of $5 \times 10^6$ per well in AIM-V medium. After incubation for 2 to 3 hours at 37° C., nonadherent cells were removed from the culture and the medium was replaced with AIM-V plus 800 units/mL granulocyte macrophage colony-stimulating factor and 500 units/mL IL-4. On days 3 and 5, half the medium was removed and replaced with AIM-V plus 800 units/mL granulocyte macrophage colony-stimulating factor and 500 units/mL IL-4. A mix of maturation cytokines (1 µmol/L/mL prostaglandin E2, 1,000 units/mL tumor necrosis factor-α, and 500 units/mL IL-1β) was added on day 5 or 6. For stimulation of CD8+ T cells specific for HLA-A2.1-binding SCCE peptide epitopes, mature dendritic cells were collected after maturation for 48 hours, and pulsed with 50 µg/mL of peptide for 2 hours in AIM-V at 37° C. The dendritic cells were then washed once with AIM-V medium and used for T cell stimulation at a peripheral blood mononuclear cell/dendritic cell ratio of 30:1. After 7 days, T cells were collected and restimulated with peptide-pulsed dendritic cells. After the second stimulation, CD8+ T cells were recovered by positive selection with anti-CD8 magnetic beads (Dynal Biotech, Brown Deer, Wis.). During the second and third T cell stimulation and passage, 50 to 100 units/mL IL-2 was added to the medium, and T cells were periodically fed (every 2-3 days) by changing 50% to 70% of the medium and addition of fresh IL-2. Further passaging of CD8+ T cell lines used peptide-loaded autologous peripheral blood lymphocytes as antigen-presenting cells.

For stimulation of SCCE peptide-specific CD4+ helper T cell and CD8+ CTL responses, 50 µg/mL of the appropriate SCCE peptide was added to dendritic cells on days 5 or 6 (at the time of addition of maturation mix) and the dendritic cells were harvested 48 hours later. Initial T cell stimulation was the same as described above. After the second stimulation, CD4+ and CD8+ T cells were recovered by positive selection with anti-CD4 or anti-CD8 magnetic beads (Dynal). During the second and subsequent T cell passages, 20 to 50 units/mL IL-2 was added to the medium, and the cultures were periodically fed (every 2-3 days) by changing 50% to 70% of the medium and addition of fresh IL-2. Dendritic cells were used as antigen-presenting cells for the first three to five antigen stimulations. Later antigen stimulations were done with autologous lymphoblastoid cell lines pulsed overnight with 50 µg/mL SCCE peptide.

Cytotoxicity Assays.

Standard $^{51}$Cr-release assays were done as described previously (17). Autologous lymphoblastoid cell lines were pulsed with 50 µg/mL of appropriate CTL peptide, or left unpulsed. Lymphoblastoid cell lines were pulsed overnight with 50 µg/mL of extended SCCE peptide at 37° C. in AIM-V medium, whereas dendritic cells were pulsed with 50 µg/mL peptide for 48 hours during final maturation. Peptide-pulsed targets were then labeled with 50 µCi Na$_2$[$^{51}$Cr]O$_4$ for an additional hour and washed three times before use. K562 cells, which are sensitive to natural killer cell lysis, were labeled similarly with $^{51}$Cr. Blocking antibodies were added to target cells at concentrations indicated for each assay immediately prior to plating. Target cells were plated at $1 \times 10^4$ per well in 96-well round-bottomed plates with effector T cells at the ratios indicated for each assay. Assays were done in triplicate wells. The percentage of target cell lysis was calculated as described (17).

Cytokine Assays.

Intracellular cytokine expression was measured by flow cytometry after overnight coculture of T cells with peptide-pulsed or unpulsed lymphoblastoid cell lines, dendritic cells, or tumor cell lines. T cells ($1.5 \times 10^6$) were plated in 12-well Costar plates in 2 mL RPMI/10 Hu. T cells were stimulated with phorbol 12-myristate 13-acetate (50 ng/mL) and ionomycin (500 ng/mL) as a positive control. Negative controls included T cells cultured alone, or with unpulsed lymphoblastoid cell lines or dendritic cells. At the onset of coculture, 10 µg/mL of Brefeldin A was added to block cytokine release. Cells were collected after the overnight stimulation and fixed in 2% paraformaldehyde in PBS for 10 minutes at room temperature. The cells were washed once in PBS and again in 0.5% saponin and 1% bovine serum albumin in PBS. T cells were labeled with cytokine-specific MAb conjugated to PE or FITC for 30 minutes at room temperature. After staining, the cells were washed twice in 0.5% saponin and 1% bovine serum albumin in PBS, once with 0.5% bovine serum albumin in PBS, and fixed in 2% paraformaldehyde in PBS. Fluorescence was measured with a FACSCalibur (Becton Dickinson, San Jose, Calif.) and data were analyzed with WinMDI software.

2B. Results

Three peptides were selected from the sequence of SCCE as having clusters of possible HLA class II protein binding segments. The peptides were residues 1-23, 61-84, and 143-160 of SCCE.

The peptides were prepared by chemical synthesis and loaded onto dendritic cells as described above in Materials and Methods.

Figure 1B:
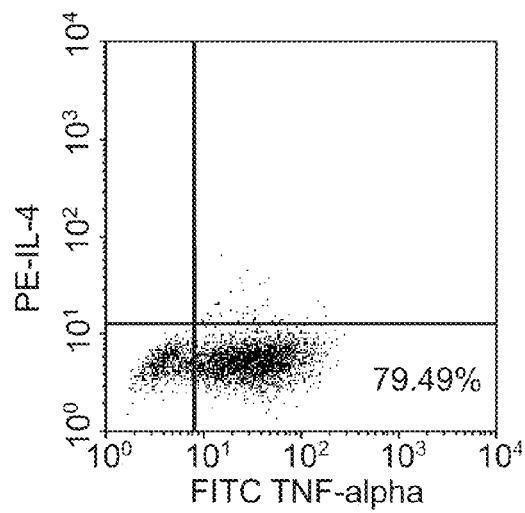
Figure 1C:
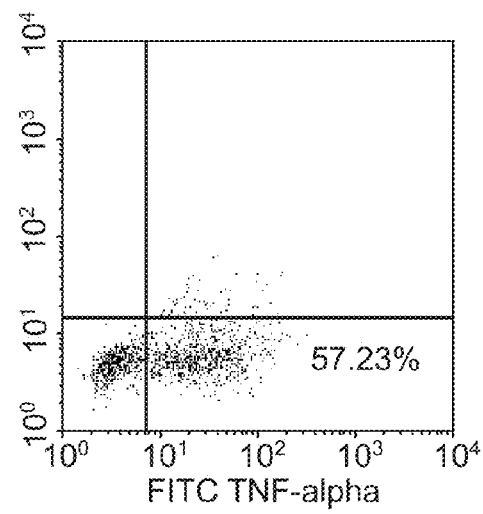

CD4+ T cells were amplified as described above in Materials and Methods with the peptide-loaded dendritic cells. The amplified CD4+ T cells were tested for secretion of the cytokines TNF-alpha and IL-4 when stimulated with autologous LCL loaded with the peptide used to amplify the CD4+ T cells. Secretion of the cytokines was monitored by flow cytometry, and the results are shown in FIG. 1. All three of the peptides stimulated cytokine expression. The CD4+ cells were stimulated to release TNF-α but not IL-4.

CD8+ T cells amplified with the three tested SCCE peptides were tested for ability to lyse target LCL pulsed with the corresponding peptide. Lysis was tested against autologous LCL as well as allogeneic LCL matched in specific HLA class I alleles. The results are shown in FIG. 1. All three of the peptides stimulated lysis of autologous LCL pulsed with the peptide. Peptide 1-23 also stimulated lysis of HLA B27-matched allogeneic LCL. Peptide 61-84 stimulated lysis of HLA A2.1-matched LCL. Peptide 143-160 stimulated lysis of HLA-A2.1-matched LCL.

Results of further cytokine secretion assays are shown in Table 1.

TABLE 1

CD4+ T cell cytokine secretion in response to SCCE peptides.

| Peptide | Donor | HLA-DR type | Cytokine | Stimulator cells | Percent secreting cells |
|---|---|---|---|---|---|
| 1-23 | MDC | DR15, DR17, DR51, DR52 | TNF-α | Control LCL | 3% |
|  |  |  |  | LCL + peptide | 21% |
|  | MJC | DR3, DR52 | TNF-α | Control LCL | 3% |
|  |  |  |  | LCL + peptide | 6% |
| 61-84 | MJC | DR3, DR52 |  | Control LCL | <1% |
|  |  |  | TNF-α | LCL + peptide | 75% |
|  |  |  | Interferon-gamma | LCL + peptide | 30% |
|  |  |  | IL-2 | LCL + peptide | 30% |
| 143-160 | MJC | DR3, DR52 | IL-2 | LCL control | 1% |
|  |  |  |  | LCL + peptide | 6-11% |

2C. Conclusions

All three extended SCCE peptides tested stimulated CD4+ T cell proliferation and cytokine secretion from each of the donors tested. Peptide 1-23 was tested with one donor and peptides 61-84 and 143-160 were tested with two donors. CD8+ T cells amplified with each of the three extended SCCE peptides also lysed autologous target cells pulsed with the peptide in a peptide-specific manner.

Example 2. Hepsin Peptides

Hepsin is a transmembrane serine protease that is overexpressed in prostate cancer and ovarian cancer, as well as renal cell carcinoma (19-26). In at least one report its overexpression was linked to metastasis and tumor progression (21). In this Example the hepsin sequence (SEQ ID NO:2) was scanned to identify regions predicted to have multiple epitopes that bind to a variety of HLA class II allelic proteins. Peptides containing the predicted epitopes were synthesized and used to amplify CD4+ and CD8+ T cells and the response of the amplified T cells to the peptides was tested.

Results:

The sequence of hepsin was processed using the algorithms described in Example 1 to identify epitopes predicted to bind to HLA class II alleles DRB1*0401, DRB1*0101, and DRB1*0701. Peptides were synthesized corresponding to sequences in hepsin predicted to have multiple epitopes that bind to at least two of those three HLA class II allelic proteins. The selected peptides were residues 48-84, 90-117, 177-210, 214-236, 226-250, and 255-287 of hepsin.

The peptides were loaded onto dendritic cells, and the peptide-loaded dendritic cells were used to amplify CD4+ T cells and CD8+ T cells as described in Example 1. The amplified CD4+ T cells were tested for cytokine secretion in response to stimulation by peptide-loaded LCL. The results are shown in Table 2. All of the hepsin peptides stimulated cytokine secretion from CD4+ T cells stimulated with autologous peptide-loaded cells. Tumor necrosis factor alpha (TNF-α) was the cytokine whose secretion was stimulated the most. Interferon, interleukin-2, and interleukin-4 secretion were also stimulated.

TABLE 2

CD4+ T cell cytotokine secretion in response to hepsin peptides.

| Peptide | Donor | HLA DR type | Cytokine | Stimulator cells | Percent secreting cells |
|---|---|---|---|---|---|
| 48-84 | MDC | DR15, DR17, DR52, DR53 | TNF-α | Control LCL | 3% |
|  |  |  |  | LCL + peptide | 34% |
|  | MJC | DR3, DR52 | various | Control LCL | 1-3% |
|  |  |  | TNF-α | LCL + peptide | 32% |
|  |  |  | Interferon-gamma | LCL + peptide | 9% |
|  |  |  | IL-2 | LCL + peptide | 6% |
|  |  |  | IL-4 | LCL + peptide | 4% |
| 90-117 | MDC | DR15, DR17, DR51, DR52 | TNF-α | Control LCL | 2% |
|  |  |  |  | LCL + peptide | 16% |
|  | MJC | DR3, DR52 | various | Control LCL | 1-6% |
|  |  |  | TNF-α | LCL + peptide | 38% |
|  |  |  | Interferon | LCL + peptide | 30% |
|  |  |  | IL-2 | LCL + peptide | 13% |
|  |  |  | IL-4 | LCL + peptide | 7% |
| 177-210 | 976 | DR1, DR7 | various | Control LCL | 1% |
|  |  |  | TNF-α | LCL + peptide | 54% |
|  |  |  | Interferon | LCL + peptide | 4% |
|  |  |  | IL-2 | LCL + peptide | 9% |
|  |  |  | IL-4 | LCL + peptide | 7-9% |
|  | 819 | DR4, DR13 | various | Control LCL | 0% |
|  |  |  | TNF-α | LCL + peptide | 13% |
|  |  |  | Interferon | LCL + peptide | 27% |
|  |  |  | IL-2 | LCL + peptide | 1% |
| 255-287 | 976 | DR1, DR7 | various | Control LCL | 0-1% |
|  |  |  | TNF-α | LCL + peptide | 37% |
|  |  |  | Interferon | LCL + peptide | 16% |
|  |  |  | IL-2 | LCL + peptide | 5% |
|  |  |  | IL-4 | LCL + peptide | 10-11% |
|  | MJC | DR3, DR52 | TNF-α | Control LCL | 0% |
|  |  |  |  | LCL + peptide | 10% |
| 214-236 | 666 | DR1, DR8 | TNF-α | Control LCL | 2% |
|  |  |  |  | LCL + peptide | 21% |
|  | 679 | DR4, DR7 | various | Control LCL | 0% |
|  |  |  | TNF-α | LCL + peptide | 49% |
|  |  |  | Interferon | LCL + peptide | 10% |
|  |  |  | IL-2 | LCL + peptide | 27% |
|  |  |  | IL-4 | LCL + peptide | 10% |

The CD4+ T cells were also tested for cytotoxicity against peptide-loaded target cells. The results are shown in Table 3. Each of the peptides tested amplified CD4+ T cells from every donor tested, and the amplified CD4+ T cells showed peptide-specific cytolysis of autologous cells loaded with the peptide.

TABLE 3

CD4+ T cell cytotoxicity against hepsin peptide-loaded target cells.

| Peptide | Donor | HLA-DR type | Target cells | Percent cell killing. |
|---|---|---|---|---|
| 48-84 | MJC | DR3, DR52 | LCL control | 4% |
| | | | LCL + peptide | 42% |
| 90-117 | MJC | DR3, DR52 | LCL | 6% |
| | | | LCL + peptide | 65% |
| 396-412 | MJC | DR3, DR52 | LCL | 12% |
| | | | LCL + peptide | 22% |
| 214-236 | 666 | DR1, DR8 | LCL | 3.5% |
| | | | LCL + peptide | 13% |
| 226-250 | 679 | DR4, DR7 | LCL | 17% |
| | | | LCL + peptide | 35% |

CD4+ T cells are the helper T cells that function primarily to activate and control the immune response of other immune cells including antibody-producing cells and CD8+ cytotoxic T cells. CD8+ T cells are the cells primarily responsible for cytolysis of target tumor cells. The ability of peptide-amplified CD8+ T cells to lyse target cells was also assayed, and the results are shown in Table 4. Each of the six tested peptides amplified CD8+ T cells that were cytotoxic against autologous cells loaded with the peptide.

TABLE 4

CD8+ T cell cytotoxicity against hepsin peptide-loaded target cells.

| Peptide | Donor | HLA Class I type | Target cells | Percent cell killing. |
|---|---|---|---|---|
| 48-84 | MDC | A2, B8, B27 | autologous LCL control | 3% |
| | | | autologous LCL + peptide | 21% |
| | | | A2-matched allogeneic LCL + peptide | 42% |
| | | | B27-matched allogeneic LCL + peptide | 31.3% |
| | | | B61/B51-matched allogeneic LCL + peptide | 27.1% |
| | | | complete mismatched LCL + peptide | 1.8% |
| 90-117 | MDC | A2, B8, B27 | autologous LCL | 2.5% |
| | | | autologous LCL + peptide | 11.6% |
| | MJC | A1, A2, B8, B27 | autologous LCL | 3% |
| | | | autologous LCL + peptide | 9% |
| 396-412 | MJC | A1, A2, B8, B27 | autologous LCL | 45% |
| | | | autologous LCL + peptide | 65% |
| 177-210 | 976 | A2, A3, B13, B65 | autologous LCL | 7.3% |
| | | | autologous LCL + peptide | 21.3% |
| 214-236 | 666 | A2, A3, B35, B51 | autologous LCL | 6% |
| | | | autologous LCL + peptide | 30% |
| 226-250 | 679 | A2, A23, B27, B60 | autologous LCL | 2.2% |
| | | | autologous LCL + peptide | 20% |

Conclusions:

Every hepsin extended peptide tested amplified CD4+ cells that were stimulated by autologous cells loaded with the peptide. The stimulated CD4+ cells released TNF-α and interferon, and lesser amounts of IL-2 and IL-4. Each of the peptides also amplified CD4+ that showed peptide-specific cytotoxicity against autologous cells from various donors loaded with the peptide. Six of the peptides were tested for their ability to stimulate CD8+ cells that were cytotoxic to autologous cells loaded with the peptide. Each of the six tested peptides generated CD8+ T cells that showed peptide-specific killing of autologous cells.

Example 3. Matriptase Peptides

Matriptase (also known as TADG-15) is a transmembrane serine protease that was discovered in 1993 and cloned in 1999 (3, 7). It is overexpressed in many tumors of epithelial origin, including carcinomas of the head and neck, mesothelium, breast, ovary, cervix, prostate, lung, and gastrointestinal tract, as well as in cell lines derived from these tumors (8). Its expression has been linked to increased tumor invasiveness (5-6). It is expressed in a high percentage of ovarian carcinomas but not in normal ovary tissue (4). Matriptase's pattern of overexpression in many tumors makes it an attractive target for immunotherapy in ovarian and other cancers. The importance of matriptase expression in prostate cancer progression has been emphasized by studies showing that a selective matriptase inhibitor inhibits growth of androgen-independent human prostate tumor xenografts in nude mice (6). Furthermore, overexpression of matriptase in the skin of transgenic mice resulted in spontaneous squamous cell carcinoma, suggesting a causal role for matriptase in epithelial cancers (27).

The sequence of matriptase was processed using the algorithms described in Example 1 to identify epitopes predicted to bind to HLA class II alleles DRB1*0401, DRB1*0101, and DRB1*0701. Peptides were synthesized corresponding to sequences in matriptase predicted to have multiple epitopes that bind to at least two of those three HLA class II allelic proteins. The selected peptides were residues 170-204, 273-296, 308-343, and 379-399.

The peptides were loaded onto dendritic cells, and the peptide-loaded dendritic cells were used to amplify CD4+ T cells and CD8+ T cells as described in Example 1. The amplified CD4+ T cells were tested for cytokine secretion in response to stimulation by peptide-loaded LCL. The results are shown in Table 5. All of the peptides stimulated release of at least TNF-α in each donor tested, which in some cases was one donor and in other cases two donors.

TABLE 5

CD4+ T cell cytotokine secretion in response to matriptase peptides.

| Peptide | Donor | HLA-DR type | Cytokine | Stimulator cells | Percent secreting cells |
|---|---|---|---|---|---|
| 170-204 | 976 | DR1, DR7 | various | Control LCL | 1-2% |
| | | | TNF-α | LCL + peptide | 23% |
| | | | Interferon- | LCL + peptide | 6% |

TABLE 5-continued

CD4+ T cell cytotokine secretion in response to matriptase peptides.

| Peptide | Donor | HLA-DR type | Cytokine | Stimulator cells | Percent secreting cells |
|---|---|---|---|---|---|
| | | | gamma IL-2 | LCL + peptide | 15% |
| | | | IL-4 | LCL + peptide | 7-8% |
| | MJC | DR3, DR52 | various | Control LCL | 1-2% |
| | | | TNF-α | LCL + peptide | 16% |
| | | | Interferon | LCL + peptide | 6% |
| 273-296 | 976 | DR1, DR7 | TNF-α | Control LCL | 5%% |
| | | | | LCL + peptide | 9% |
| 308-343 | 976 | DR1, DR7 | various | Control LCL | 0.5-1% |
| | | | TNF-α | LCL + peptide | 23% |
| | | | Interferon | LCL + peptide | 7% |
| | | | IL-2 | LCL + peptide | 10% |
| | | | IL-4 | LCL + peptide | 5-6% |
| | MJC | Dr3, DR52 | TNF-α | Control LCL | 3% |
| | | | TNF-α | LCL + peptide | 19% |
| | | | Interferon | Control LCL | 1% |
| | | | Interferon | LCL + peptide | 3% |
| 379-399 | 976 | DR1, DR7 | various | Control LCL | 2-10% |
| | | | TNF-α | LCL + peptide | 60% |
| | | | Interferon | LCL + peptide | 7% |
| | | | IL-2 | LCL + peptide | 4% |
| | | | IL-4 | LCL + peptide | 1-2% |

The ability of the peptides to amplify CD8+ T cells that lysed target cells loaded with the peptide was also assayed. The results are shown in Table 6. Only the peptide 170-204 was assayed. It generated CD8+ T cells that displayed peptide-specific cytolysis against LCL loaded with the peptide.

TABLE 6

CD8+ T cell cytotoxicity against matriptase peptide-loaded target cells.

| Peptide | Donor | HLA Class I type | Target cells | Percent cell killing |
|---|---|---|---|---|
| 170-204 | 976 | A2, A3, B13, B65 | autologous LCL control | 13% |
| | | | autologous LCL + peptide | 59% |
| | | | A3-matched allogeneic LCL + peptide | 29% |
| | | | B13-matched allogeneic LCL + peptide | 0% |
| | | | A2-matched allogeneic LCL + peptide | 0% |
| | | | complete mismatched LCL + peptide | 0% |
| | MJC | A1, A2, B8, B27 | autologous LCL control | 0% |
| | | | autologous LCL + peptide | 6% |

Conclusion:

All of the matriptase peptides tested stimulated CD4+ T cell cytokine secretion. The one peptide tested for CD8+ cytotoxic response, 170-204, amplified CD8+ T cells that showed peptide-specific cytolysis against cells loaded with the peptide.

Example 4. Infusing Dendritic Cells Loaded with a Matriptase, Hepsin, or SCCE Peptide to Treat Ovarian Cancer Ovarian cancer patients having tumors positive for expression of matriptase, hepsin, or SCCE are treated in this Example. Patients undergo leukopheresis using a COBE separator. Peripheral blood leukocytes (PBL) from the patients are used for generation of dendritic cells (DC). Monocyte-derived DC are cultured in AIM-V (Gibco-BRL) supplemented with GM-CSF and IL-4 as described in Example 1. After 5 days' culture, DC maturation is induced by addition of TNFα, IL-1β, and $GPE_2$, as described in Example 1. At the time of induction of maturation, one or more matriptase, hepsin, and/or SCCE peptides is also added, at a concentration of 50 μg/ml of each peptide. The cells are incubated for 48 hours to mature and process the peptides. The DC are then washed twice to remove unbound peptides. The DC are then suspended in PBS supplemented with 10% autologous serum, and infused intravenously into the patient over a period of one hour. Typically, all of the DC that could be obtained are infused into the patient.

Patients receive a total of five treatments at three-week intervals.

The treated patients are observed to have less tumor growth, more tumor shrinkage, or longer remissions than comparable patients who do not receive the treatment.

The sequences of SCCE, hepsin, and matriptase that were used to select peptides are as shown below.

Stratum Corneum Chymotryptic Enzyme, SEQ ID NO:1, accession no. AAC37551.

```
  1 marslllplq illlslalet ageeaqgdki idgapcargs hpwqvallsg nqlhcggvlv
 61 nerwvltaah ckmneytvhl gsdtlgdrra qrikasksfr hpgystqthv ndlmlvklns
121 qarlssmvkk vrlpsrcepp gttctvsgwg tttspdvtfp sdlmcvdvkl ispqdctkvy
181 kdllensmlc agipdskkna cngdsggplv crgtlqglvs wgtfpcgqpn dpgvytqvck
241 ftkwindtmk khr
```

Hepsin, SEQ ID NO:2, accession no. AAC37551.

```
  1 magkeggrtv pccsrpkvaa ltagtllllt aigaaswaiv avllrsdqep lypvqvssad 61 arlmvfdkte gtwrllcssr snarvaglsc eemgflralt hseldvrtag angtsgffcv 121 degrlphtqr llevisvcdc prgrflaaic qdcgrrklpv drivggrdts lgrwpwqvsl 181 rydgahlcgg sllsgdwvlt aahcfpernr vlsrwrvfag avagasphgl qlgvqavvyh 241 ggylpfrdpn seensndial vhlssplplt eyiqpvclpa aggalvdgki ctvtgwgntq 301 yygqqagvlq earvpiisnd vcngadfygn qikpkmfcag ypeggidacq gdsggpfvce 361 dsisrtprwr lcgivswgtg calaqkpgvy tkvsdfrewi fqaikthsea sgmvtql
```

Matriptase, SEQ ID NO:3, accession no. AAG15395.

```
  1 mgsdrarkgg ggpkdfgagl kynsrhekvn gleegveflp vnnvkkvekh gpgrwvvlaa 61 vliglllvll gigflvwhlq yrdvrvqkvf ngymritnen fvdayensns tefvslaskv 121 kdalkllysg vpflgpyhke savtafsegs viayywsefs ipqhlveeae rvmaeervvm 181 lpprarslks fvvtsvvafp tdsktvqrtq dnscsfglha rgvelmrftt pgfpdspypa 241 harcqwalrg dadsvlsltf rsfdlascde rgsdlvtvyn tlspmephal vqlcgtypps 301 ynltfhssqn vllitlitnt errhpgfeat ffqlprmssc ggrlrkaqgt fnspyypghy 361 ppnidctwni evpnnqhvkv sfkffyllep gvpagtcpkd yveingekyc gersqfvvts 421 nsnkitvrfh sdqsytdtgf laeylsydss dpcpgqftcr tgrcirkelr cdgwadctdh 481 sdelncscda ghqftcknkf ckplfwvcds vndcgdnsde qgcscpaqtf rcsngkclsk 541 sqqcngkddc gdgsdeascp kvnvvtctkh tyrclnglcl skgnpecdgk edcsdgsdek 601 dcdcglrsft rgarvvggtd adegewpwqv slhalgqghi cgaslispnw lvsaahcyid 661 drgfrysdpt qwtaflglhd qsqrsapgvq errlkriish pffndftfdy diallelekp 721 aeyssmvrpi clpdashvfp agkaiwvtgw ghtqyggtga lilqkgeirv inqttcenll 781 pqqitprmmc vgflsggvds cqgdsggpls sveadgrifq agvvswgdgc aqrnkpgvyt 841 rlplfrdwik entgv
```

REFERENCES

1. Southwood S, Sidney J, Kondo A, et al. Several common HLA-DR types share largely overlapping peptide binding repertoires. J Immunol 1998; 160:3363-73.
2. Parker K C, Bednarek M A, Coligan J E. Scheme for ranking potential HLA-A2 binding peptides based on independent binding of individual peptide side-chains. J Immunol 1994; 152:163-75.
3. Shi Y E, et al. Identification and characterization of a novel matrix-degrading protease from hormone-dependent human breast cancer cells. Cancer Res. 1993; 53:1409-15.
4. Tanimoto H, et al. Transmembrane serine protease TADG-15 (ST14/matriptase/MT-SP1): expression and prognostic value in ovarian cancer. Br J. Cancer. 2005; 92:278-83.
5. Suzuki M, et al. Inhibition of tumor invasion by genomic down-regulation of matriptase through suppression of activation of receptor-bound prourokinase. J Biol Chem. 2004; 279:14899-908.
6. Galkin A V, et al. CVS-3983, a selective matriptase inhibitor, suppresses the growth of androgen independent prostate tumor xenografts. Prostate. 2004; 61:228-235.
7. Lin C Y, Anders J, Johnson M, Sang Q A, Dickson R B. Molecular cloning of cDNA for matriptase, a matrix-degrading serine protease with trypsin-like activity. J Biol Chem. 1999; 274:18231-6.
8. List, K., T. H. Bugge, R. Szabo. 2006. Matriptase: potent proteolysis on the cell surface. Mol. Med. 12:1-7.
9. Cannon M J, O'Brien T J, Underwood L J, Crew M D, Bondurant K L, Santin A D. Novel target antigens for dendritic cell immunotherapy of ovarian cancer. Expert Rev Anticancer Ther 2002; 2:89-97.
10. Santin A D, Cane' S, Bellone S, Bignotti E, Palmieri M, De Las Casas L E, Roman J J, Anfossi S, O'Brien T, Pecorelli S. The serine protease stratum corneum chymotryptic enzyme (kallikrein 7) is highly overexpressed in squamous cervical cancer cells. Gynecol Oncol. 2004 August; 94(2):283-8.
11. Schuler G, Schuler-Thurner B, Steinman R M. The use of dendritic cells in cancer immunotherapy. Curr Opin Immunol 2003; 15:138-47.
12. Gilboa E. The promise of cancer vaccines. Nat Rev Cancer 2004; 4:401-11.
13. Santin A D, Hermonat P L, Ravaggi A, Pecorelli S, Cannon M J, Parham G P. Induction of tumor-specific HLA class I-restricted CD8+ cytotoxic T lymphocytes by ovarian tumor antigen-pulsed autologous dendritic cells in patients with advanced ovarian cancer. Am J Obstet Gynecol 2000; 183:601-9.
14. Santin A D, Hermonat P L, Ravaggi A, et al. Induction of tumor-specific CD8+ cytotoxic T lymphocytes by tumor lysate-pulsed autologous dendritic cells in patients with serous papillary uterine cancer. Br J Cancer 2002; 86:151-7.
15. Tanimoto H, Underwood L J, Shigemasa K, et al. The stratum corneum chymotryptic enzyme which mediates shedding and desquamation of skin cells is highly overexpressed in ovarian tumor cells. Cancer 1999; 86:2074-82.
16. Santin A D, Bellone S, Ravaggi A, Pecorelli S, Cannon M J, Parham G P. Induction of ovarian tumor-specific CD8+ cytotoxic T lymphocytes by acid-eluted peptide-pulsed autologous dendritic cells. Obstet Gynecol 2000; 96:422-30.
17. Nazaruk R A, Rochford R, Hobbs M V, Cannon M J. Functional diversity of the CD8+ T cell response to Epstein-Barr virus: Implications for the pathogenesis of EBV-associated lymphoproliferative disorders. Blood 1998; 91:3875-83.
18. Rammensee H-G, Friede T, Stevanovic S. MHC-ligands and peptide motifs: first listing. Immunogenetics 1995; 41:178-228.
19. Tanimoto H., Yan Y, Clarke J., Korourian S., Shigemasa K., Parmley T. H., Parham G. P., O'Brien T. J. Hepsin, a cell surface serine protease identified in hepatoma cells, is overexpressed in ovarian cancer. Cancer Res. 1997; 57:2884-2887.
20. Dhanasekaran, S. M.; Barrette, T. R.; Ghosh, D.; Shah, R.; Varambally, S.; Kurachi, K.; Pienta, K. J.; Rubin, M. A.; Chinnaiyan, A. M. Delineation of prognostic biomarkers in prostate cancer. Nature (London). 2001; 412:822-826.
21. Klezovitch O., Chevillet J., Mirosevich J., Roberts R. L., Matusik R. J., Vasioukhin V. Hepsin promotes prostate cancer progression and metastasis. Cancer Cell. 2004; 6:185-195.
22. Magee, J. A.; Araki, T.; Patil, S.; Ehrig, T.; True, L.; Humphrey, P. A.; Catalona, W. J.; Watson, M. A.; Milbrandt, J. Expression profiling reveals hepsin overexpression in prostate cancer. Cancer Res. 2001; 61:5692-5696.
23. Stamey, T. A.; Warrington, J. A.; Caldwell, M. C.; Chen, Z.; Fan, Z.; Mahadevappa, M.; McNeal, J. E.; Nolley, R.; Zhang, Z. Molecular genetic profiling of Gleason grade 4/5 prostate cancers compared to benign prostatic hyperplasia. J. Urol. 2001; 166:2171-2177.
24. Adib, T. R.; Henderson, S.; Perrett, C.; Hewitt, D.; Bourmpoulia, D.; Ledermann, J.; Boshoff, C. Predicting biomarkers for ovarian cancer using gene-expression microarrays. Br. J. Cancer. 2004; 90:686-692.
25. Stephan C., Yousef G. M., Scorilas A., Jung K., Jung M., Kristiansen G., Hauptmann S., Kishi T., Nakamura T., Loening S. A., Diamandis E. P. Hepsin is highly over expressed in and a new candidate for a prognostic indicator in prostate cancer. J. Urol. 2004; 171:187-191.
26. Zacharski, L. R.; Ornstein, D. L.; Memoli, V. A.; Rousseau, S. M.; Kisiel, W. Expression of the factor VII activating protease, hepsin, in situ in renal cell carcinoma. Thromb. Haemostasis. 1998; 79:876-877.
27. List K, Szabo R, Molinolo A, Sriuranpong V, Redeye V, Murdock T, Burke B, Nielsen B S, Gutkind J S, Bugge T H. (2005) Deregulated matriptase causes ras-independent multistage carcinogenesis and promotes ras-mediated malignant transformation. *Genes Dev.* 19:1934-1950.

All patents, patent documents, and other references cited herein are incorporated by reference.

What is claimed is:

1. A composition comprising:
   purified dendritic cells loaded ex vivo with a purified peptide of 7-50 amino acid residues comprising an antigenic matriptase sequence of 7-50 amino acid residues;
   wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the matriptase sequence.

2. The composition of claim 1 wherein when the purified peptide is contacted with dendritic cells to generate peptide-loaded dendritic cells and the peptide-loaded dendritic cells are contacted with T cells, the peptide-loaded dendritic cells amplify CD8+ T cells (cytotoxic T lymphocytes, CTL) that recognize the matriptase sequence.

3. The composition of claim 2 wherein the amplified CD8+ T cells kill autologous cancer cells expressing matriptase.

4. The composition of claim 1 wherein the peptide can be used with dendritic cells to activate CD4+ T cells from at least two donors with no HLA class II alleles in common.

5. The composition of claim 1 wherein the purified peptide comprises SEQ ID NO:4 (residues 170-204 of SEQ ID NO:3), SEQ ID NO:5 (residues 273-296 of SEQ ID NO:3), SEQ ID NO:6 (residues 308-343 of SEQ ID NO:3), or SEQ ID NO:7 (residues 379-399 of SEQ ID NO:3.

6. A composition of matter comprising:
   purified dendritic cells loaded ex vivo with a purified peptide comprising an antigenic matriptase sequence of at least 7 amino acid residues;
   wherein when the purified peptide is contacted with dendritic cells to generate peptide-loaded dendritic cells and the peptide-loaded dendritic cells are contacted with T cells, the peptide-loaded dendritic cells amplify CD4+ T cells (helper T cells) that recognize the matriptase sequence.

7. The composition of matter of claim 6 wherein the peptide can be used with dendritic cells to activate CD4+ T cells from at least two donors with no HLA class II alleles in common.

8. The composition of matter of claim 6 wherein the purified peptide is a purified peptide of 50 or fewer amino acid residues comprising SEQ ID NO:4 (residues 170-204 of SEQ ID NO:3), SEQ ID NO:5 (residues 273-296 of SEQ ID NO:3), SEQ ID NO:6 (residues 308-343 of SEQ ID NO:3), or SEQ ID NO:7 (residues 379-399 of SEQ ID NO:3.

* * * * *